United States Patent [19]

Daily

[11] Patent Number: 5,609,620
[45] Date of Patent: Mar. 11, 1997

[54] CARDIAC COOLING JACKET

[75] Inventor: Pat O. Daily, 16560 El Camino Real, Rancho Santa Fe, Calif. 92067

[73] Assignee: Pat O. Daily, San Diego, Calif.

[21] Appl. No.: 467,565

[22] Filed: Jun. 6, 1995

(Under 37 CFR 1.47)

[51] Int. Cl.⁶ .................................................. A61F 7/00
[52] U.S. Cl. .......................................... 607/105; 607/114
[58] Field of Search .................................. 607/104–105, 607/113–114, 108, 96

[56] References Cited

U.S. PATENT DOCUMENTS

| 4,947,843 | 8/1990 | Wright et al. | 607/96 |
| 4,971,056 | 11/1990 | Seacord | 607/104 |
| 5,014,695 | 5/1991 | Benak et al. | 607/105 |
| 5,476,490 | 12/1995 | Silver | 607/108 |

*Primary Examiner*—Angela D. Sykes
*Assistant Examiner*—Ryan Carter
*Attorney, Agent, or Firm*—Baker, Maxham, Jester & Meador

[57] ABSTRACT

A flexible thermal jacket of a generally thin flat arcuate configuration having a thermal transfer face and a thermal insulating face comprises, a first thin flat sheet of impervious material having an arcuate inner and outer edge, a second sheet substantially identical to said first sheet bonded to the first sheet along the arcuate edges and along lines defining an elongated serpentine passages throughout the jacket, and a generally circular insulating tab formed of inner and outer impervious sheets and an inner thermal sheet secured to the inner edge and operative to close and or cover an opening formed by forming the jacket into a frusto-conical configuration.

16 Claims, 3 Drawing Sheets

CARDIAC COOLING JACKET

BACKGROUND OF THE INVENTION

The present invention relates to medical devices and pertains particularly to an improved cardiac cooling jacket.

Open heart surgery is carried out with the heart deprived of the flow of blood for at least a short period of time. It is desirable to reduce the metabolism of the heart during the surgery in order to reduce potential damage. A typical technique for reducing the metabolism is to reduce the temperature of the organ.

Various techniques have been used in the past for reducing the temperature of an organ during surgery. One of the preferred methods of reducing the temperature is to wrap the organ in a cooling jacket through which a cold fluid is circulating. An early example of a cooling jacket is disclosed in U.S. Pat. No. 4,154,245 entitled "Apparatus for Local Hypothermia". A later and preferred form of cooling jacket for heart surgery is disclosed in U.S. Pat. No. 4,071,056 granted Nov. 15, 1990, both of common assignment herewith.

While the current designs for cooling jackets have been satisfactory, they do have some drawbacks. One drawback of the current design is that under certain circumstances, they do not fully insulate the organ from the patients body. The usual procedure is to wrap the cooling jacket around the organ and rest it on the patients body. The current design frequently leaves an opening for direct contact of the organ with the patients body with a resulting transfer of heat from the body to the organ.

Therefore, there is a need for an improved cooling jacket that fully insulates the organ from the patients body.

SUMMARY OF THE INVENTION

It is a primary object of the present invention to provide an improved cooling jacket for heart surgery that fully insulates the heart from the patients body during surgery.

In accordance with a primary aspect of the present invention, a cooling jacket comprises flexible thermal pad of a generally thin flat arcuate configuration having a thermal transfer face and a thermal insulating face comprises, a first thin flat sheet of impervious material having an arcuate inner edge and a arcuate outer edge, a second sheet substantially identical to said first sheet bonded to said first sheet along said arcuate edges and along lines defining elongated serpertine fluid passages throughout said pad, and a generally circular insulating tab formed of inner and outer impervious sheets and an inner thermal sheet secured to said inner edge and operative to substantially close an opening formed by arranging said pad into a frusto-conical configuration.

BRIEF DESCRIPTION OF THE PREFERRED EMBODIMENTS

The above and other objects and advantages of the present invention will become apparent from the following description when read in conjunction with the accompanying drawings wherein.

DETAILED DESCRIPTION OF THE PREFERRED EMBODIMENTS

Figure 1:
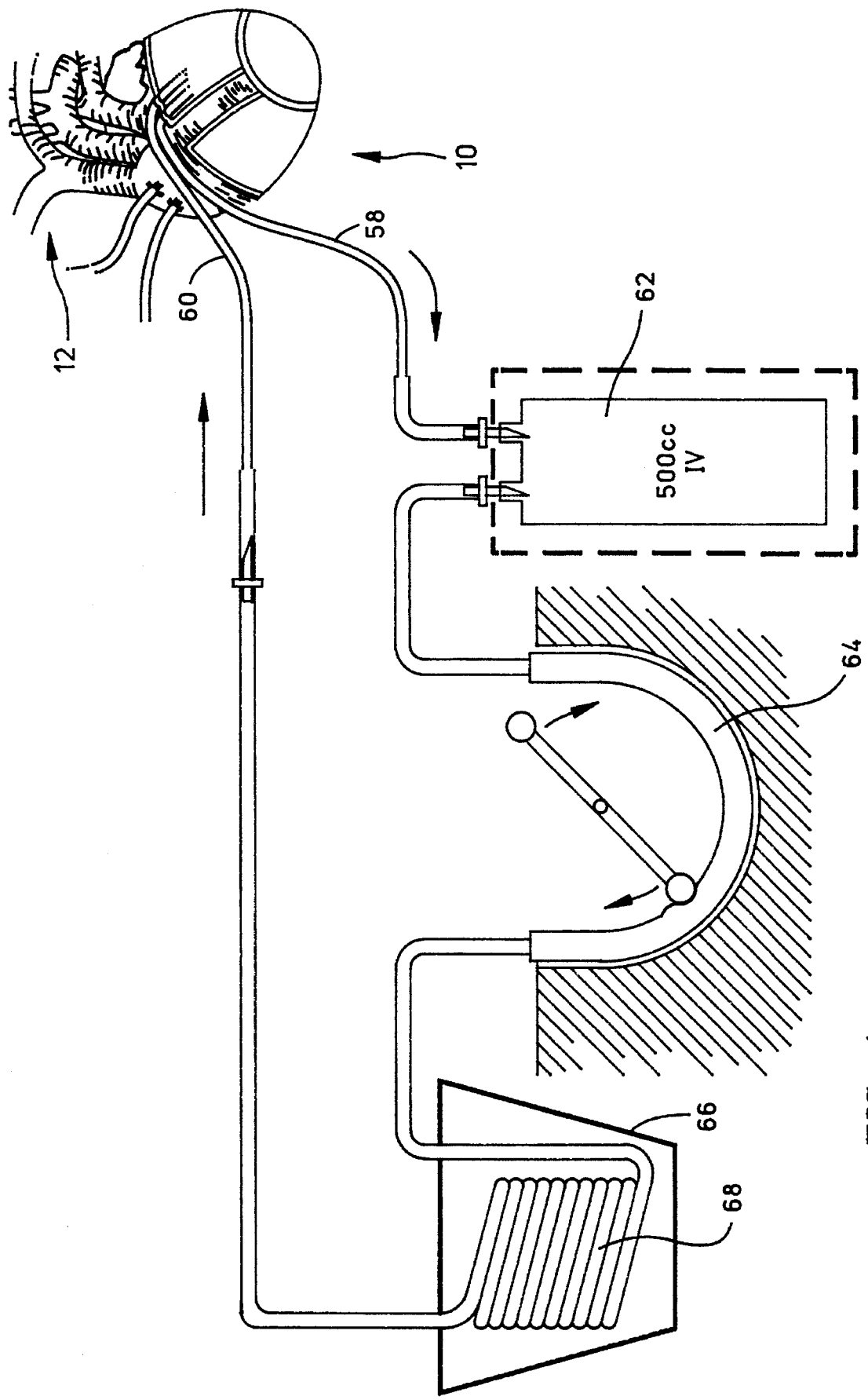
FIG. 1 is a diagrammatic illustration of a cooling jacket in accordance with a preferred embodiment of the present invention the present invention show in use.

Referring to FIG. 1 of the drawings, there is illustrated a cooling jacket in accordance with the invention, designated generally by the numeral 10, shown formed in a cup or bowl shape in position underneath and containing a heart designated generally at 12. The cooling jacket 10 is wrapping around the heart for applying hypothermia thereto. The cooling jacket, as illustrated in FIG. 2, has an arcuate or fan shape, such that when rolled it forms a frustrum of a cone, thereby forming a cup shape configuration encompassing the heart as shown in FIG. 1.

The cooling jacket is also provided with inlet and outlet tubes or ports 14 and 16, (FIG. 2) which are at one end and extend outward from the outermost curved edge of the jacket for connecting into a cooling fluid circulating system to be described. The placement of these inlet and outlet ports or cooling fluid supply and return tubes at one end, and at the outside diameter of the jacket leaves the remainder of the jacket unobstructed. This places the tubes out of the way to enable the jacket to be inserted and slipped beneath the heart and the free end wrapped around the heart. The tubes are thus placed in a position where they do not interfere with placement of the jacket in and around the heart.

Figure 2:
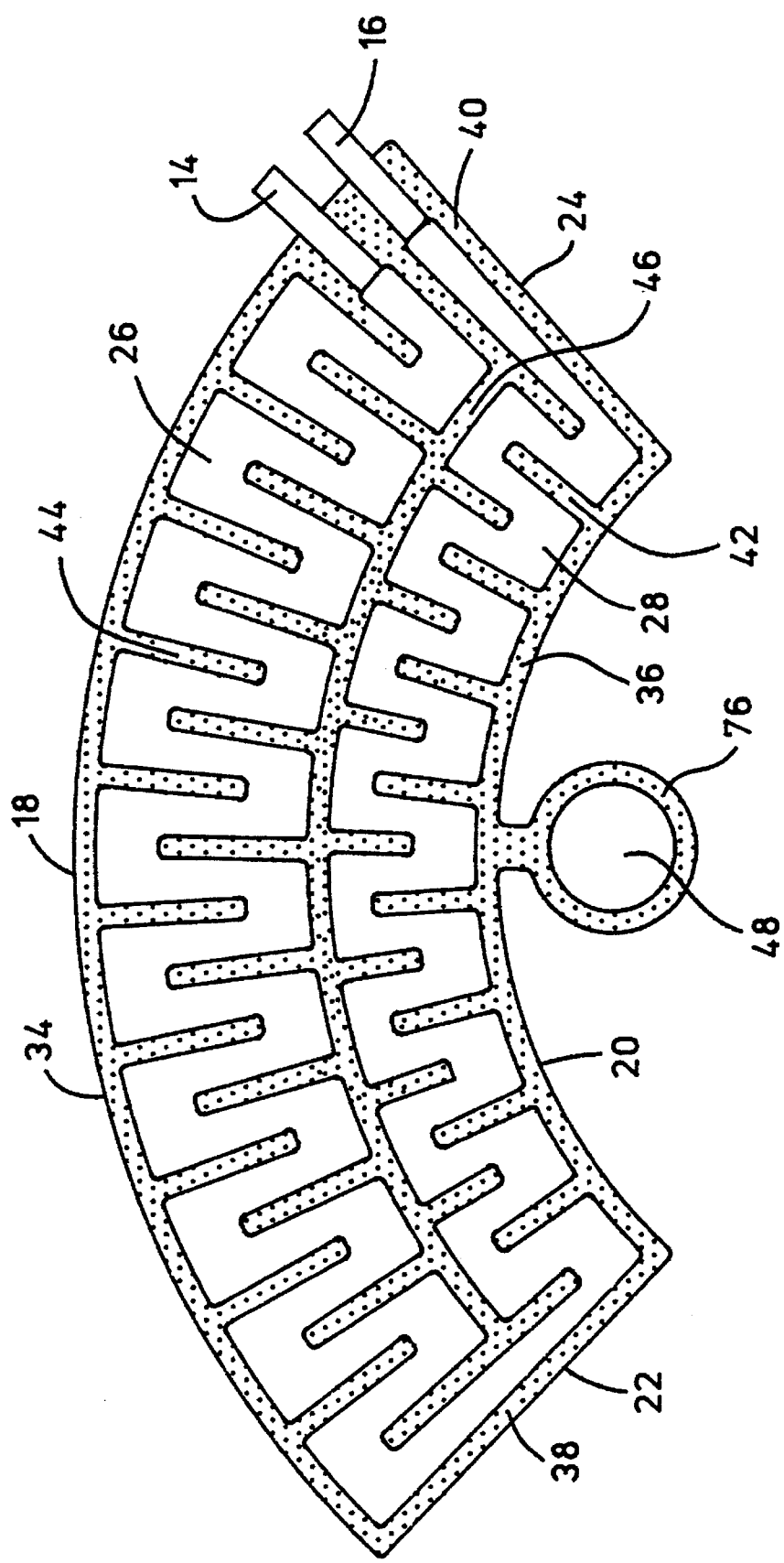
FIG. 2 is top plan view of the embodiment of FIG. 1.

The jacket 10, as best seen in FIG. 2, is thin and flat and of an arcuate or fan shape, having an outer and arcuate edge 18 and an inner arcuate edge 20, with a left radial edge 22 and a right radial edge 24. This shape of the jacket enables it to be rolled in a bowl or cuplike frusto-conical configuration to best fit the shape of the heart and contain the heart and provide maximum and most efficient contact therewith. The cooling jacket with this configuration can be more closely conformed to the shape of the lower portion of the heart, as illustrated.

Figure 3:
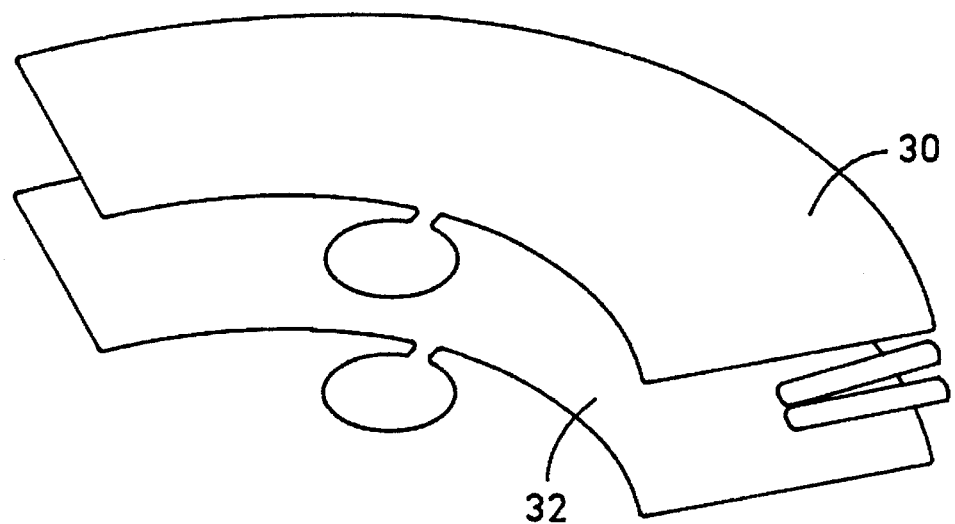
FIG. 3 is an exploded perspective view of sheets forming the fluid circuit assembly.

Referring to FIG. 2, the jacket or pad has an upper cooling surface with underlying serpentine cooling fluid channels extending throughout the cooling face or surface. The jacket is formed with supply and return channels with, for example, a supply channel 26 being formed with a zig-zag pattern or series of alternate U-shaped channels extending from the inlet port 14 into return channel 28 also having a zig-zag pattern of alternate U-shaped channels. This portion of the jacket defines a thermal or heat transfer face or surface. The fluid flow channels are formed between a pair of thin film panels 30 and 32, as shown in FIG. 3. They are secured together by heat sealing seams or welds 34, 36, 38, and 40 along the peripheral edges and along patterns defining the flow channels. These flow channels are o formed by a plurality of inwardly extending fingers, line welds or seams 42, extending outward from seam weld 36 along the inner edge or diameter 20. Similar finger or line welds 44 extend inward from the outer edge 18.

A central arcuate weld 46 with alternating fingers extends across the jacket from between the inlet and outlet ports 14 and 16 and at the edge 24 over to the adjacent edge 22. This forms alternating channels across the length of the pad, alternating between the supply and return channel. This serpentine array of the supply and return fluid passages or channels provides a more uniform temperature distribution across the cooling face of the channel. The results are adjacent counter flow channels that maintain a more uniform temperature across the entire face of the jacket.

An important feature of the jacket is a round or circular insulating flap or closure 48 formed or secured at the inner edge 20. This closure can be pivoted and cover or close an opening normally formed or resulting wrapping the jacket around an organ as shown in FIG. 1. This closure is formed by tabs formed on the face and back panels, as will be explained.

Figure 4:
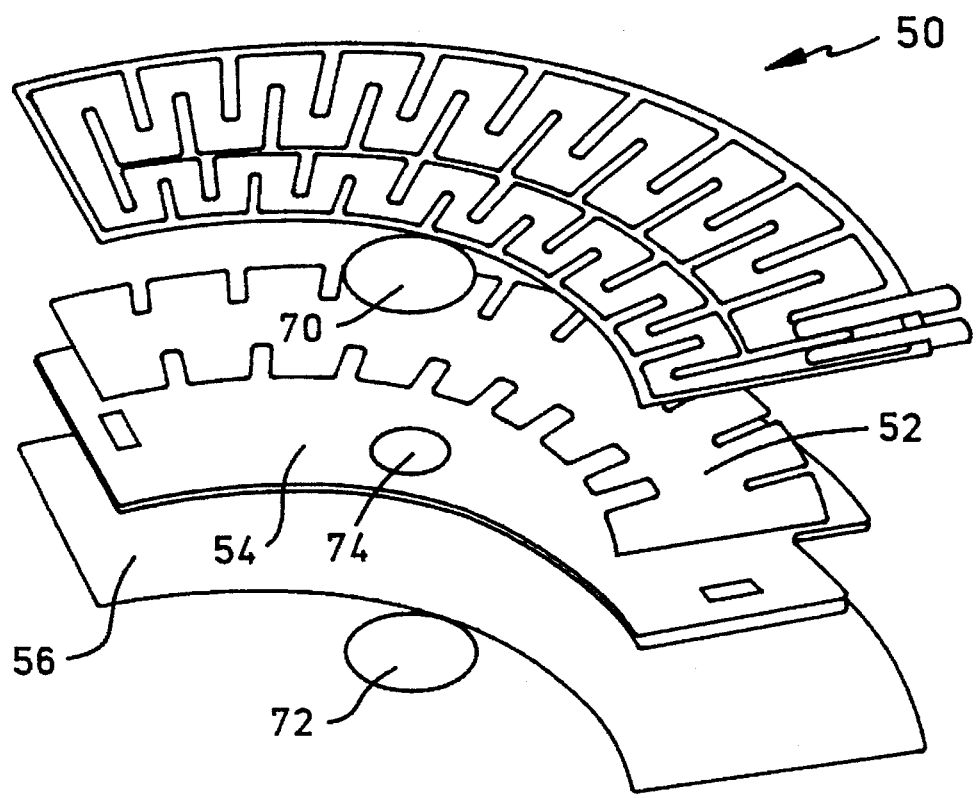
FIG. 4 is a exploded perspective assembly view of the embodiment of FIG. 1.

Referring to FIG. 4 of the drawings, there are illustrated details of the structure and steps of construction of the jacket in accordance with the invention. In accordance with the invention, as illustrated, the cooling jacket is made up of a plurality of layers, as will be described. The cooling jacket comprises, as illustrated, a top sheet or panel, designated generally by the numeral 50, made up of sheets 30 and 32, as explained above. This panel 50 has the characteristic fan or arcuate shape and is constructed of sheets of a suitable pliable impervious material, such as a good medical grade of silicone or urethane, preferably on the order of about two to six mils in thickness. This forms the heat transfer face and may be plain or it may have the characteristic weld pattern as illustrated. A second or backing sheet 32 of a similar size, shape and material, as the top cover is placed beneath the cover, and is provided with tubes 14 and 16 defining the inlet and outlet ports at one end.

In the process of assembly of the top cover 50, sheet 30 is placed over the bottom sheet 32, with the tubing joints 14 and 16 in position and an RF 2 welder is applied to weld the top and bottom covers together along the inner and outer arcuate edges 18 and 20, and along the inner weld lines as illustrated, thereby forming face panel and the cooling fluid channels in the jacket.

A backbone member 52, which is preferably formed of a thin sheet of aluminum or the like, for example, on the order on the order of about thirty-two thousandth of an inch in thickness, can be shaped and retain its shape to support the jacket in a selected position or shape. This sheet 52 preferably has slots that overlie finger welds 42 and 44 that extend from the inner and outer arcuate edges 18 and 20. This backbone is selected and assembled behind or beneath the back or second sheet of cover 50, with a foam insulating pad 54 of the characteristic arcuate shape then selected and placed over and behind the backbone 52. A backing cover 56 of substantially the same characteristic, size and shape as the first back or acing cover 50 is selected and placed over or behind the backbone and foam padding 54. The cover 56 is slightly larger than the foam insulating pad 54 and is welded along the perimeter or peripheral edge to the cover 50, encasing the backbone 52 and the insulating pad 54. The insulating pad 54 may be of any suitable insulating foam having a thickness of on the order of about 10–40 mils. The jacket may be formed in selected sizes for use on different size hearts.

The closure flap 48 is formed from a round or circular flap 70 on the top panel 50 and flap 72 on backing sheet 56. A circular disc 74 of insulating foam is sandwiched between the flaps 70 and 72 which are welded together along seam 76.

In use, a cooling jacket of an appropriate size is selected and placed around the heart 12, as shown in FIG. 1, and is connected to a source of circulating cooling fluid, as illustrated. The jacket forms a frusto-conical shaped cup or bowl around the heart with closure flap 48 pivoted over to cover any opening at the bottom formed as shown in FIG. 1. The jacket is connected by means of lines or tubes 58 and 60, which may be in a closed loop, for example, with a reservoir 62, pump 64, a cooling unit or ice pack, including an ice bucket 66 and cooling coil 68, and with suitable means for adjusting the coolant flow. A suitable fluid may be a sterile saline solution contained in a standard I.V. bag and immersed in an ice water bath. A suitable pump circulates the cooling fluid though the system.

While I have illustrated and described my invention by means of specific embodiments, it is to be understood that numerous changes and modifications may be made therein without departing from the spirit and the scope of the invention as defined in the appended claims.

I claim:

1. A flexible thermal jacket of a generally thin flat arcuate configuration having a thermal transfer face and a thermal insulating face comprising:

a first thin flat sheet of impervious material having an arcuate inner edge and a arcuate outer edge, said inner edge being of lesser diameter than said outer edge;

a second sheet substantially identical to said first sheet bonded to said first sheet along said arcuate edges and along lines defining elongated serpentine fluid passages throughout said pad; and, a generally circular insulating closure tab formed of inner and outer impervious sheets and an inner insulating sheet secured to said inner edge and operative to substantially close an opening formed by said inner edge upon arranging said pad into a frusto-conical configuration.

2. A jacket according to claim 1 wherein said first and second sheets are bonded along an arcuate line substantially centrally between said edges and along alternate finger lines extending alternately from said central line and said arcuate edges.

3. A jacket according to claim 2 further comprising:

a backing sheet; and an insulating sheet between said second sheet and said backing sheet.

4. A jacket according to claim 3 further comprising a malleable plate disposed between said second sheet and said backing sheet.

5. A jacket according to claim 4 further comprising an insulating sheet between said malleable plate and said backing sheet.

6. A jacket according to claim 1 further comprising:

a backing sheet; and an insulating sheet between said second sheet and said backing sheet.

7. A jacket according to claim 6 further comprising malleable plate between said second sheet and said backing sheet.

8. A jacket according to claim 6 wherein said malleable plate is sheet metal having an arcuate shape and slots extending inward from outer and inner arcuate edges at positions to overlap inwardly extending seal lines from outer and inner edges of said first and second sheets.

9. A jacket according to claim 8 wherein said closure tab comprises:

a circular tab extending from said inner arcuate edge of said cover sheet;

a circular tab extending from said inner arcuate edge of said backing sheet; and a circular insulating sheet between said cover sheet and said backing sheet.

10. A jacket according to claim 1 wherein said closure tab comprises:

a circular tab extending from said inner arcuate edge of said cover sheet;

a circular tab extending from said inner arcuate edge of said backing sheet; and a circular insulating sheet between said cover sheet and said backing sheet.

11. A flexible thermal jacket of a generally thin flat arcuate configuration having a thermal transfer face and a thermal insulating face comprising:

a first thin flat sheet of impervious material having arcuate inner and outer edges, said inner edge having lesser diameter than said outer edge;

a second sheet substantially identical to said first sheet bonded to said first sheet along said arcuate edges and along lines defining elongated serpentine passages throughout said pad;

a backing sheet formed of a thin flat sheet of impervious material having an arcuate inner and outer edges bonded along said inner and outer edges to said first and second sheets; and, a generally circular insulating tab formed of inner and outer impervious sheets and an inner thermal sheet secured to said inner edge and operative to close and or cover an opening formed by said inner edge upon forming said pad into a frusto-conical configuration.

12. A jacket according to claim 11 wherein said first and second sheets are bonded along an arcuate line substantially centrally between said edges and along alternate finger lines extending alternately from said central line and said arcuate edges.

13. A jacket according to claim 12 further comprising malleable plate between said second sheet and said backing sheet.

14. A jacket according to claim 13 wherein said malleable plate is sheet metal having an arcuate shape and slots extending inward from outer and inner arcuate edges at positions to overlap inwardly extending seal lines from outer and inner edges of said first and second sheets.

15. A flexible thermal jacket of a generally thin flat arcuate configuration having a thermal transfer face and a thermal insulating face comprising:

a heat transfer panel formed of a first thin flat sheet of impervious material having arcuate inner and outer edges, said inner edge being of lesser diameter than said outer edge, a second sheet substantially identical to said first sheet bonded to said first sheet along said arcuate edges and along lines defining an elongated serpentine passages throughout said panel between adjacent inlet and outlet ports;

a backing panel formed of a first thin flat sheet of impervious material having an arcuate inner and outer edges bonded along said inner and outer edges to said heat transfer panel; and a generally circular insulating closure tab formed of top and bottom impervious tab sheets integral with one of said first and second sheets and said backing sheets, and an inner thermal sheet sandwiched between said top and bottom tab sheets operative to cover an opening formed by said inner edge upon forming said jacket into a frusto-conical configuration.

16. A jacket according to claim 15 further comprising:

an insulating sheet between said heat transfer panel and said backing sheet; and a malleable plate between said insulating sheet and said heat transfer panel.

* * * * *

UNITED STATES PATENT AND TRADEMARK OFFICE
CERTIFICATE OF CORRECTION

PATENT NO. : 5,609,620
DATED : March 11, 1997
INVENTOR(S) : Daily

It is certified that error appears in the above-indentified patent and that said Letters Patent is hereby corrected as shown below:

On the title page, item [73] should read:

Assignee: Pat O. Daily, as trustee under the Pat O. Daily Revocable Trust 10-27-89

Signed and Sealed this

Thirteenth Day of May, 1997

*Attest:*

BRUCE LEHMAN

*Attesting Officer*   *Commissioner of Patents and Trademarks*